(12) United States Patent
Grieve et al.

(10) Patent No.: US 7,415,305 B2
(45) Date of Patent: Aug. 19, 2008

(54) METHOD FOR THE SPATIAL MAPPING OF FUNCTIONAL BRAIN ELECTRICAL ACTIVITY

(75) Inventors: Philip Grieve, New York, NY (US); Raymond I. Stark, New York, NY (US); Joseph R. Isler, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 570 days.

(21) Appl. No.: 10/956,857

(22) Filed: Oct. 1, 2004

(65) Prior Publication Data
US 2006/0074336 A1    Apr. 6, 2006

(51) Int. Cl.
*A61B 5/04* (2006.01)
(52) U.S. Cl. .................................... 600/544
(58) Field of Classification Search ............... 600/544, 600/545
See application file for complete search history.

(56) References Cited
U.S. PATENT DOCUMENTS

| | | | | |
|---|---|---|---|---|
| 5,083,571 A | * | 1/1992 | Prichep | ...................... 600/544 |
| 5,119,816 A | * | 6/1992 | Gevins | ........................ 600/383 |
| 5,381,512 A | * | 1/1995 | Holton et al. | ............ 704/200.1 |
| 5,667,470 A | * | 9/1997 | Janata | ......................... 600/28 |
| 6,907,280 B2 | * | 6/2005 | Becerra et al. | .............. 600/407 |
| 7,225,013 B2 | * | 5/2007 | Geva et al. | ................... 600/513 |
| 2001/0049480 A1 | * | 12/2001 | John et al. | .................. 600/559 |
| 2002/0107434 A1 | * | 8/2002 | Lange et al. | ................ 600/301 |

OTHER PUBLICATIONS

Grieve et al., "Spatial Correlation Of The Infant And Adult Electroencephalogram," Clinical Neurophysiology 114(2003), pp. 1594-1608.

* cited by examiner

*Primary Examiner*—Robert Nasser
*Assistant Examiner*—Karen E Toth
(74) *Attorney, Agent, or Firm*—Baker Botts L.L.P.

(57) ABSTRACT

The present invention discloses methods and systems for monitoring and evaluating brain electrical activity. Methods are provided for obtaining local synchrony information relating to regions of a brain. Methods are provided that include obtaining EEG information from an infant subject, and using the obtained EEG information in obtaining local coherence information. A mathematical technique or computer algorithm can be used to process the EEG information in order to reduce residual volume conduction error in the obtained local coherence information.

31 Claims, 13 Drawing Sheets

600

602
Left View

Right View

Back View

Front View

Top View

604
Left View

Right View

Back View

Front View

Top View

900

902

Obtain EEG information

904

Process EEG information to
obtain local synchrony
information

Obtain EEG information from an infant subject

1004

Process EEG information to obtain local synchrony information

Obtain EEG information

1104

Process EEG information to obtain local synchrony information using volume conduction artifact reduction algorithm

Obtain EEG information from an infant subject

1204

Process EEG information to obtain local synchrony information using volume conduction artifact reduction algorithm

Fig. 12

METHOD FOR THE SPATIAL MAPPING OF FUNCTIONAL BRAIN ELECTRICAL ACTIVITY

STATEMENT REGARDING FEDERALLY SPONSORED RESEARCH OR DEVELOPMENT

This invention was made with government support under grant number EB000264 awarded by the National Institutes of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

This invention relates in general to monitoring and evaluating brain electrical activity, and in particular includes methods and systems for methods for monitoring and evaluating local synchrony between adjacent or neighboring brain regions or neural sites.

EEG, or electroencephalogram, is used to provide a measure of brain electrical activity by monitoring electric potential at multiple locations on the scalp. Synchronicity of EEG waveforms at separate scalp locations can be quantified to provide a measure of synchronicity of two neural groups or regions, which can provide an indication of similarity of behavior of the neural groups or regions. There are several known methods for measuring synchronicity between waveforms, including "coherence," which is described further below, as well as the article, "Spatial Correlation of the Infant and Adult Electroencephalogram," by Philip G. Grieve, Ronald Emerson, William P. Fifer, Joseph R. Isler, and Raysmond I. Stark, Clinical Neurophysiology 114 (2003) 1594-1608, which is hereby incorporated herein by reference in its entirety. Synchronicity and coherence measurement can provide an indication of a degree of coordination of neuron activity and function in different brain areas.

Using EEG performed with a large number of scalp locations for electrode placement, it is possible, via coherence measurement, to provide a global quantitative evaluation of apparent relatedness of neural function in disjoint brain regions, such as frontal to occipital brain regions or between hemispheres of the brain. Determining local coherence between brain regions or spatially spaced neuron sites, however, has been impractical.

In theory, EEG measurements could provide a measure of EEG local coherence, a specific synchrony measure. Using EEG to determine local synchrony, however, is fraught with difficulty. Generally, EEG measurements are taken by placing a number of electrodes spaced on an adult subject's scalp. However, if the electrodes are closely spaced, as would be necessary to attempt to obtain EEG information from which local synchrony information might be obtained, volume conduction artifact due to the presence of the skull produces a spatial blurring of electrical variation. Reasons for this include the thickness of the adult skull and its poor electrical conductivity. A result of such artifact and blurring is that closely spaced electrodes on the adult scalp yield data which suggests a high degree of local synchrony, whether or not such local synchrony is present. As such, the measured adult EEG information is itself insufficient to allow determination of local synchrony.

The remaining subsections of this section include detailed discussion of aspects of the above. Subsection (a) includes a discussion of global cortical function and theoretical determination of local synchrony using EEG information. Subsection (b) includes a discussion of EEG in the context of local synchrony between spatially distributed brain neuron sites. Finally, Subsection (c) discusses includes a discussion of how volume conduction obscures local synchrony measurements attempted using prior art EEG techniques.

a. Global Cortical Function and EEG Synchrony

The cerebral cortex is the anatomical structure where the highest level of information processing occurs. It is also the source of the electrical activity of the brain that is manifested as a spatial distribution of electric potential on the scalp known as the electroencephalogram (EEG). The cortex is known to provide distributed processing of neural information in groups of neurons that are connected to other groups that are both neighboring and distant. The electrical activity of a coordinated neural group is conducted to the scalp where it produces the EEG. The EEG is measured via scalp electrodes which are connected to amplifiers. The variation of the EEG voltage over time at a measurement site is characteristic of the neural activity in close proximity to that site. Further, the similarity of behavior (i.e., synchronicity) of EEG voltage versus time waveforms at two separate scalp locations can be quantified and is indicative of the degree of similarity of behavior of the two neural groups that produced the EEG waveforms.

There are well known methods for measuring the similarity of behavior in two waveforms such as the correlation function and the correlation coefficient. Another technique is "coherence" which is a well known signal processing technique that provides a quantitative measure of the frequency dependent correlation of two waveforms, as discussed in "Spatial Correlation of the Infant and Adult Electroencephalogram," by Philip G. Grieve, Ronald Emerson, William P. Fifer, Joseph R. Isler, and Raysmond I. Stark, Clinical Neurophysiology 114 (2003) 1594-1608 (hereinafter, "Grieve, et al. (2003)"), which is hereby incorporated herein by reference in its entirety. Thus, for a given mental task, if the EEG is measured at a large number of spatial locations and the similarity of behavior over time is calculated for the EEG at one location with EEG waveforms from other locations, it is possible to provide a global (e.g., frontal to occipital or between hemispheres) quantitative description of the apparent relatedness of neural function in disjoint brain regions. This is the essence of a large field of research over the last several decades which has largely been supplanted by fMRI studies.

b. Theoretical EEG Local Synchrony Quantifies Coordinated Local Neural Activity

However, these global neural synchrony measurements do not provide insight into the functional behavior of localized groups of activated neurons. For example, this behavior is of particular interest because the cortex is organized into anatomical columns of neurons that cooperate to perform various functions. The columns are also interconnected laterally with neighboring columns to perform coordinated localized neural processing. Although the anatomical columns are on the order of 1 mm or less in diameter, larger groups of columns performing similar functions can be many cm in dimension. Quantification of local synchrony requires the measurement of the synchronized activity of neurons at a particular spatial site with nearby (e.g., mm to cm) neighboring neural groups.

The EEG theoretically provides a means of making this measurement if we can measure the average degree of synchronicity of the EEG from a particular site with the EEG collected at the immediate neighboring sites surrounding the site of interest. A high average value for local synchrony defined in this manner indicates coordinated neural activity in the local region which may be indicative of functional activation of the neurons. This is comparable to the fMRI BOLD signal which quantifies the local decrease in deoxyhemoglobin which is indicative of neural activation in a region.

c. Volume Conduction Artifact Obscures EEG Local Synchrony

Although it would appear straightforward to calculate local synchrony from EEG data, the volume conduction of current from cortical neurons to the scalp makes the accurate measurement of synchrony difficult when the EEG is measured from closely spaced leads as is required for local synchrony. The major cause of volume conduction is the poorly conducting skull which produces a spatial blurring of cortical electrical potential variation when measured with the scalp EEG. Volume conduction can cause the EEG from two closely spaced electrodes to have a high degree of synchrony even when the neural activities at the two sites are unrelated because each electrode captures electrical activity from neurons located near the other electrode. This "crosstalk" artifact causes an erroneous value for local synchrony to be calculated as it combines true synchrony with a constant component that is a function of the degree of spatial spreading of the EEG rather than being related to neural activity. This artifact component is very large for the thick-skulled adult making local synchrony measured for the adult a large constant value that is insensitive to neural activity. This is not true for the infant with a skull 5-10 times thinner than the adult. For example, at an angular electrode spacing of 0.3 radians, the mean value for the lower 10 percentile of adult coherence is 0.9 while that of the infant is 0.3 (see previously incorporated article. This means that for the adult, measured coherence values are essentially always greater than 0.9 no matter whether the neural activities are related or not. However for the infant this value is 3 times lower so that measured infant coherence values can range from 0.3 to 1.0 and are a more sensitive measure of true cortical coherence. That the adult value is 3 times that of the infant is indicative of the large volume conduction artifact present in the adult local coherence measurement.

In contrast, there is essentially no artifact from volume conduction for leads placed directly on the cortical surface. As most EEG research has been with adult subjects, the large amount of volume conduction artifact present in the adult EEG has lead researchers to believe that synchrony measurements made from closely spaced electrodes are of little value, the major finding being that the level of synchrony decreased as the lead spacing increased. This result is largely caused by volume conduction contamination of the synchrony measurements. However there have been a few investigations of coherence from closely spaced electrodes placed directly on the cortical surface of humans and animals.

For the reasons, there is a need for methods and systems for monitoring and evaluating local synchrony and local coherence between neighboring brain regions or neural sites.

SUMMARY OF THE INVENTION

In some embodiments, the invention provides methods and systems for monitoring and evaluating brain electrical activity. Methods are provided for obtaining local synchrony, or local synchrony information, relating to adjacent regions of a brain. Furthermore, methods are provided that include obtaining EEG information from an infant subject, and using the obtained EEG information in obtaining local synchrony information. In some embodiments, local coherence information is obtained as a measure of local synchrony. In some embodiments, a mathematical technique or computer algorithm can be used to process the EEG information in order to reduce residual volume conduction error in the obtained local synchrony.

In one embodiment, the invention provides a system for obtaining local synchrony information. The system includes an EEG device for obtaining EEG information, the device comprising a plurality of electrodes placed to measure a subject's brain electrical activity. The system further includes a processing device for processing the EEG information to obtain information including local synchrony information.

In another embodiment, the invention provides a method for obtaining local synchrony information. The method includes obtaining EEG information. The method further includes, using the obtained EEG information, obtaining local synchrony information.

In another embodiment, the invention provides a method for obtaining local synchrony information. The method includes obtaining EEG information from an infant subject. The method further includes using the obtained EEG information, obtaining local synchrony information.

In another embodiment, the invention provides a method for obtaining local synchrony information. The method includes obtaining EEG information. The method further includes, using the obtained EEG information, obtaining local synchrony information. Obtaining EEG information comprises using a mathematical technique to reduce residual volume conduction artifact in the obtained the local synchrony information.

In another embodiment, the invention provides a method for obtaining local synchrony information. The method includes obtaining EEG information from an infant subject. The method further includes, using the obtained EEG information, obtaining local synchrony information. Obtaining EEG information comprises using a mathematical technique to reduce residual volume conduction artifact in the obtained the local synchrony information.

In some embodiments, an infant subject can be preferable to an adult subject in that an infant generally has a much thinner skull than an adult, so that volume conduction artifact is less with an infant as compared to an adult.

Some embodiments include a mathematical technique, algorithm, or computer algorithm for reducing residual volume conduction artifact. The algorithm may use one or more coherence functions. Reduction of residual volume conduction artifact can increase accuracy of obtained local synchrony and can effectively increase sensitivity systems for obtaining such information.

In some embodiments, a multiple electrode device is used that includes many (for example, 100 or more) electrodes for close spacing on a scalp (3 centimeters apart or less).

In some embodiments, the local synchrony comprises or is obtained from local synchrony information.

In some embodiments, the local synchrony is used as an indicator or, or to evaluate, brain function. The local coherence measurement information may be in spatial mapping of local regional brain activity.

In some embodiments, the systems are used in conducting scientific research, in conducting medical research, in medical diagnosis.

BRIEF DESCRIPTION OF THE DRAWINGS

The invention is illustrated in the figures of the accompanying drawings which are meant to be exemplary and not limiting, in which like references are intended to refer to like or corresponding parts, and in which:

FIG. 9 is a flow chart according to one embodiment of the invention;

FIG. 10 is a flow chart according to another embodiment of the invention;

FIG. 11 is a flow chart according to another embodiment of the invention;

FIG. 12 is a flow chart according to another embodiment of the invention; and

DETAILED DESCRIPTION OF THE PREFERRED EMBODIMENTS

In the following description of the preferred embodiments, reference is made to the accompanying drawings that form a part hereof, and in which is shown by way of illustration a specific embodiment in which the invention may be practiced. It is to be understood that other embodiments may be utilized and structural changes may be made without departing from the scope of the present invention.

The following article discuss EGG techniques, and each is hereby incorporated herein by reference in its entirety: "Quantitative Analysis of Spatial Sampling Error in the Infant and Adult Electroencephalogram," by Philip G. Grieve, Ronald Emerson, Joseph R. Isler and Raysmond I. Stark, *Neuroimage* 21(4) (2004):1260-74, received 22 May 2003, revised 22 Nov. 2003, accepted 25 Nov. 2003.

In some embodiments, methods and systems of the present invention include obtaining local synchrony information. "Local synchrony information," as used herein, includes information that provides a quantitative measure of local synchrony, in which adjacent electrodes (or other means for obtaining electrical activity measurement at a site) used in calculating the quantitative measure are spaced no more than 3 centimeters apart. In some embodiments, local coherence is used as a measure of local synchrony.

As discussed in detail in the Background section herein, while EEG information has been used to determine apparent global coherence information relating to a brain, as discussed in the Background section herein, local synchrony or local synchrony information has not been obtainable due to volume conduction artifact caused by thick and poorly conductive adult skull. However, methods and systems according to embodiments of the present invention allow reduction of volume conduction artifact relative to prior art techniques, and thereby allow obtaining local synchrony information.

Local synchrony can be used in spatial mapping of local brain function as indicated by the local synchrony, and can be of great value in investigating and understanding brain function as well as changes in brain function. Furthermore, local synchrony can be used for any number of purposes, including research, medical, diagnostic, and commercial uses. Moreover, analysis using accurate local synchrony information, if such information was available, could itself uncover uses for the information, such as by exposing or allowing determination of correlations between the local synchrony information and, for example, medical conditions or diseases.

Figure 1:
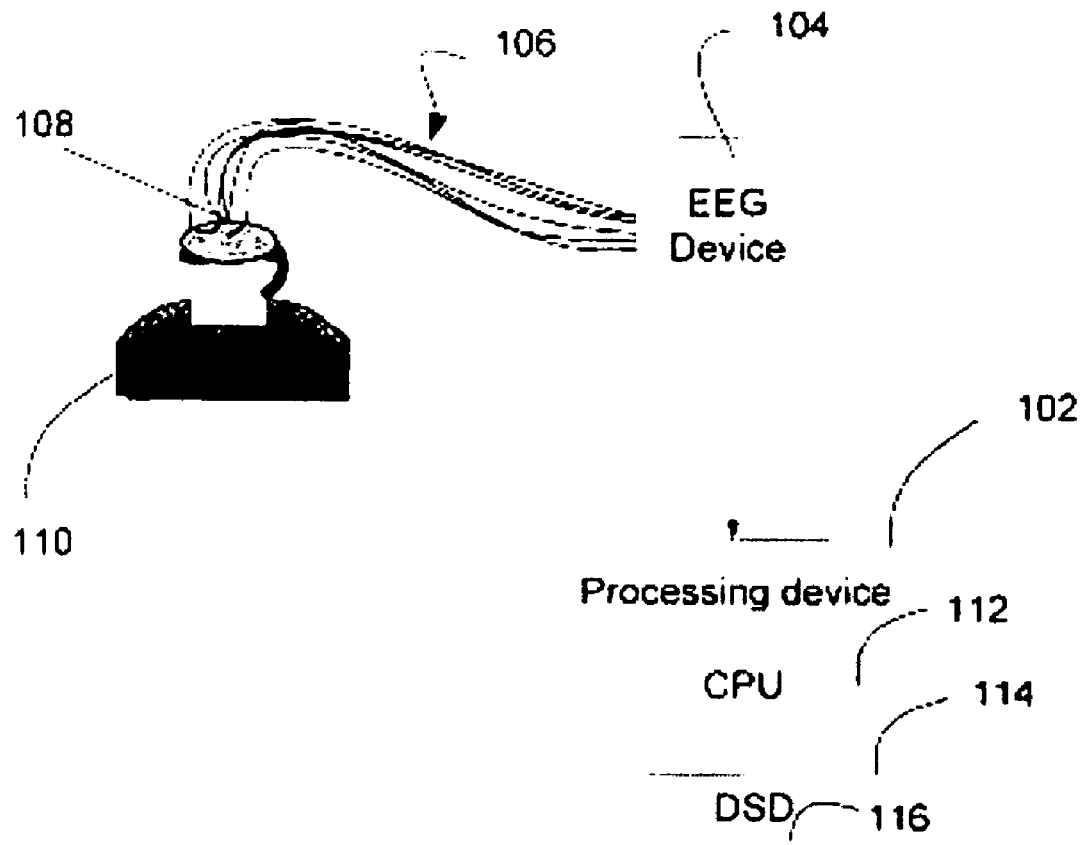
FIG. 1 is a block diagram depicting a system according to one embodiment of the invention.

FIG. 1 is a block diagram depicting a system 100 according to one embodiment of the invention. The system includes an EEG device 104 for obtaining EEG information from a subject via leads ending with electrodes 108 placed on different locations of the scalp of a subject 110 (the subject need not be part of the system 100). The EEG device 104 is connected with a processing device 102. The processing device 102 can be a computational or computerized device, such as a computer as depicted. The processing device 102 includes one or more CPUs 112 and one or more data storage devices 114. The data storage device 114 contains an artifact reduction algorithm 116. The subject 110 can be an infant, and the EEG device, including the electrodes 108 can be adapted to be used with an infant subject. Although depicted separately, in some embodiments, the EEG device 104 and the processing device 102, or their functions, can be incorporated into a single device.

In some embodiments, the invention uses a mathematical technique for reducing volume conduction artifact. The mathematical technique can be employed using a computer algorithm (such as computer algorithm 116 as depicted in FIG. 1). In some embodiments, the mathematical technique or computer algorithm is especially useful when used in conjunction with EEG information obtained from an infant subject.

In some embodiments of the invention, a multiple electrode device containing a large number of electrodes (100 or more), and channels, is used. In some embodiments, the electrodes are arrayed in a geodesic formation and are spaced no more than 3 centimeters apart from each other. Such multiple electrode device is available, for example, from Electrical Geodesics, Inc.

In some embodiments, coherence can be a statistical signal processing method that provides a frequency dependent, quantitative measure of the correlated (i.e. synchronous) activity between two time series two EEG waveforms. Although the coherence algorithm produces both a magnitude and phase difference, the phase difference measured from closely spaced leads is essentially zero, so one can restrict attention to the magnitude, normalized between 0 and 1. A large coherence value may indicate related activity at the two neighboring sites that is the result either of a driver-follower relationship or a coordinated effort driven by a third source. Coherence has been used to examine the relationship between spontaneous EEG activities made at relatively large distances. However it has been widely thought that coherence, measured between closely spaced EEG leads, is chiefly an artifact of the overlap in the "fields of view" of the leads and not a sensitive measure of related neural activity. In keeping with this view, the major effect found was simply a reduction in coherence as the spacing of the leads increased. However, it has been found that coherence measured from closely spaced leads (i.e. 1 cm) does provide information about the cortical activity when the leads are placed directly on the cortex. The difference in these conclusions is a result of the minimal spatial blurring of the EEG when collected from the cortical surface as compared to the EEG collected from leads placed on the scalp. The blurring results from the spread of current flow from EEG cortical sources and is largely caused by the skull, which is a poor conductor. Thus the EEG collected directly from the cortical surface avoids the effects of the skull, has minimal spatial blurring, and is sensitive to the relatedness of cortical activity in closely spaced cortical regions.

In contrast, in accordance with some embodiments of the invention, the thin skull of the infant produces considerably less coherence artifact from the volume conduction of current as compared to the adult with a much thicker skull (1 mm vs. 8 mm). Furthermore, a mathematical technique is herein described can that reduce the remaining coherence artifact resulting from volume conduction. Thus, in the infant, it is possible to measure the spatial relatedness of the electrical activity of the developing cortex, with the scalp EEG, but with a sensitivity approaching that obtained from electrodes placed on the cortical surface. This advance enables a quantitative measure of local cortical neural connectivity to be measured in the infant.

It is well known that the cerebral cortex is organized into 6 layers of specialized neurons. Briefly, specialized neurons, the pyramidal cells, are organized into spatial columns. Pyramidal cell dendrites and axons as well as other specialized neurons provide cross connections between neighboring cortical columns. Further local cross connections are provided through white matter tracts underlying the cortex. Local regions are connected by long-range white matter tracts to distant regions. Adult coherence measurements are able to quantify the neural interconnection of widely separated regions but have not been able to measure localized relationships because of the obscuration caused by the large amount of volume conduction present. In fact, there has been a lower bound on the coherence measured from closely spaced leads which precludes measuring small coherence values in the adult (Grieve, et al., (2003)). However the reference also shows that the reduced volume conduction in the infant allows measurement of the coherence of cortical activity between closely spaced electrodes thus quantifying the degree of local cortical relatedness.

In some embodiments, to quantify the regionalized relationship of neural activity in the infant cortex, one can define a measure of local coherence, in some embodiments, as the average of all coherence measurements made between each scalp electrode and its nearest neighbors. The close electrode spacing required for this measurement requires that the scalp EEG be collected with a large number of electrodes. Hence an array of, for example, 128 electrodes covering the entire scalp of the infant could be used. It should be kept in mind that, in some embodiments, of the invention, electrodes are used to cover only a portion of the scalp, and to determine coherence or average coherence for a portion of the brain, for example.

Figure 2:
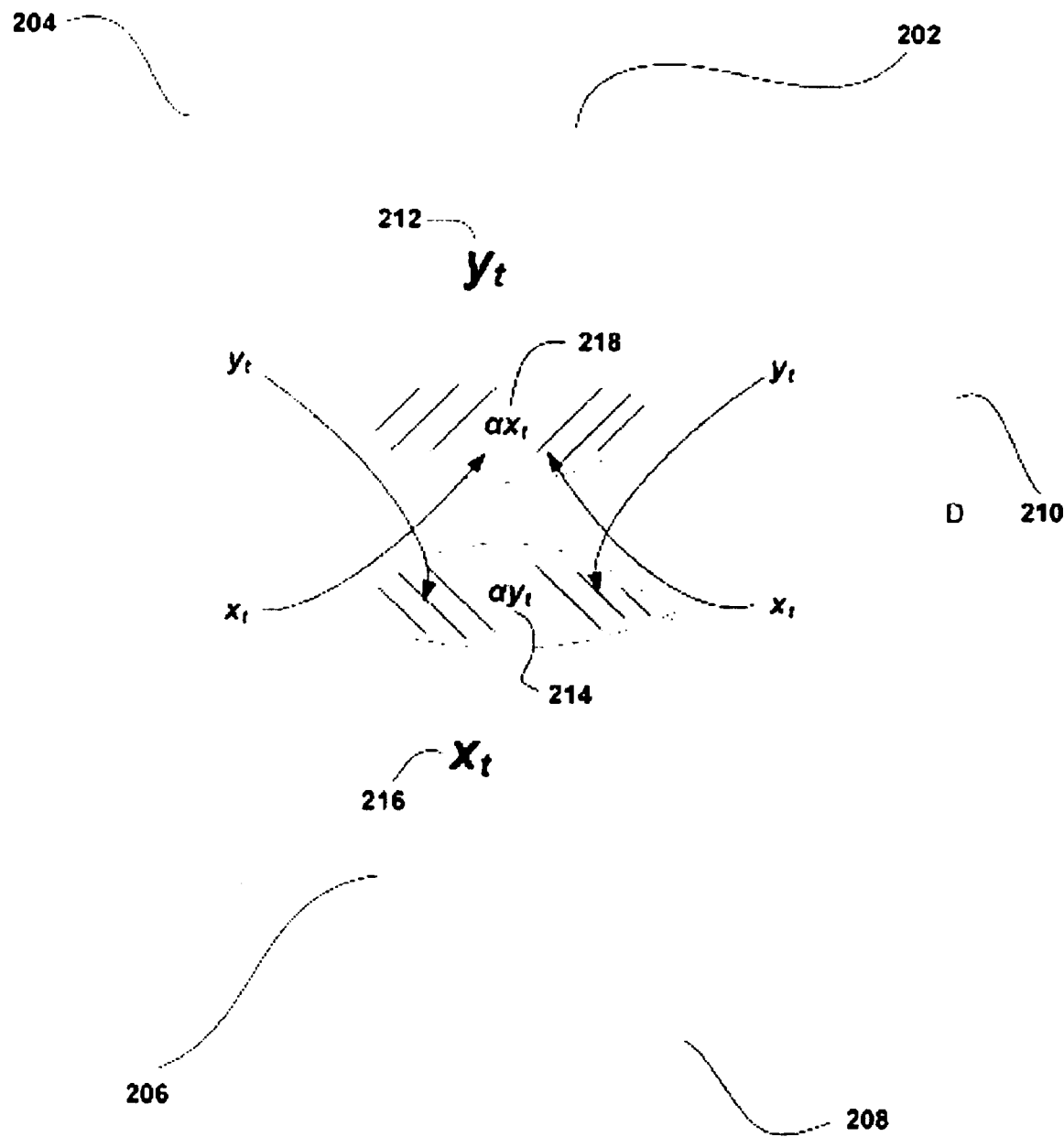
FIG. 2 is a block diagram illustrating a conceptual example of reduced volume conduction artifact in EEG information obtained from an infant subject that can be used in determining local synchrony, according to one embodiment of the invention.

FIG. 2 is a block diagram illustrating a conceptual example of reduced volume conduction artifact in EEG information obtained from an infant subject relative to that which might be obtained from an adult subject, according to one embodiment of the present invention.

Although it would appear straightforward to calculate local synchrony from EEG data, the volume conduction of current from cortical neurons to the scalp makes the accurate measurement of synchrony difficult when the EEG is measured from closely spaced leads as is required for local synchrony. The major cause of volume conduction is the poorly conducting skull which produces a spatial blurring of cortical electrical potential variation when measured with the scalp EEG. Volume conduction can cause the EEG from two closely spaced electrodes to have a high degree of synchrony even when the neural activities at the two sites are unrelated because each electrode captures electrical activity from neurons located near the other electrode. This "crosstalk" artifact causes an erroneous value for local synchrony to be calculated as it combines true synchrony with a constant component that is a function of the degree of spatial spreading of the EEG rather than being related to neural activity.

This artifact component is very large for the thick-skulled adult making local synchrony measured for the adult a large constant value that is insensitive to neural activity. This is not true for the infant with a skull 5-10 times thinner than the adult. For example, at an angular electrode spacing of 0.3 radians, the mean value for the lower 10 percentile of adult coherence is 0.9 while that of the infant is 0.3 (Grieve, et al. (2003)). This means that for the adult, measured coherence values are essentially always greater than 0.9 no matter whether the neural activities are related or not. However for the infant this value is 3 times lower so that measured infant coherence values can range from 0.3 to 1.0 and are a more sensitive measure of true cortical coherence. That the adult value is 3 times that of the infant is indicative of the large volume conduction artifact present in the adult local coherence measurement. In contrast, there is essentially no artifact from volume conduction for leads placed directly on the cortical surface.

As most EEG research has been with adult subjects, the large amount of volume conduction artifact present in the adult EEG has lead researchers to believe that synchrony measurements made from closely spaced electrodes are of little value, the major finding being that the level of synchrony decreased as the lead spacing increased. This result is largely caused by volume conduction contamination of the synchrony measurements.

Specifically, with reference to FIG. 2, a first electrode 202 is positioned at region 204 of an infant subject's scalp. A second electrode 206 within region 208 is placed adjacent to electrode 202, whereby both electrodes are separated by a finite distance (D), as defined by 210. By positioning electrode 202 at region 204, neurological electrical activity such as electroencephalogram (EEG) signals are received from an area of the brain corresponding to region 204. Similarly, positioning electrode 206 at region 208 may enable the reception of electroencephalogram (EEG) signals from an adjacent area of the brain associated with region 208. For example, electrode 202 receives the EEG signal as a time-varying voltage $(y_t)$ 212 from region 204 associated with the cerebral cortex of the brain. Also, electrode 206 receives the EEG signal as a time-varying voltage $(x_t)$ 216 from region 208.

However, the subject's skull, which is a poor electrical conductor, is a major anatomical structure that lies between the brain and the surface of the subject's scalp where the EEG signal is detected. Based on the thickness of the skull, the electrical potential generated by the neurological activities in a particular region (e.g., region 204) may be spatially diffused as it passes through the skull to the surface of the scalp; the thicker the skull, the greater the diffusion and resultant measurement obscuring.

Although electrode 202 receives time-varying voltage $(y_t)$ 212 from region 204, a fraction of this time-varying voltage $(y_t)$ 212, as defined by voltage $(\alpha y_t)$ 214, may diffuse into adjacent region 206 as a result of EEG signal spatial diffusion during propagation through the skull. Voltage $(\alpha y_t)$ 214 may then be received by adjacent electrode 206, which may cause interference with the measured time-varying voltage $(x_t)$ 216 from region 208. Thus, if voltage $(\alpha y_t)$ 214 is significant in magnitude, it may mask detected voltage $(x_t)$ 216, such that any changes in voltage $(x_t)$ 216 may remain undeterminable.

Similarly, electrode 206 receives time-varying voltage $(x_t)$ 216 from region 208, whereby a fraction of this time-varying voltage $(x_t)$ 216, as defined by voltage $(\alpha x_t)$ 218, diffuses into adjacent region 204 based on signal diffusion through the skull. Voltage $(\alpha x_t)$ 218 may then be received by adjacent electrode 202, which may cause interference with the measured time-varying voltage $(y_t)$ 212 from region 204. Thus, if voltage $(\alpha x_t)$ 218 is significant in magnitude, it may also mask voltage $(y_t)$ 216, such that any changes in voltage $(y_t)$ 212 may remain undeterminable. In this manner, adjacent signal cross talk between electrodes inhibits the determination of signal synchrony between adjacent regions of the brain's cerebral cortex. This is known as volume conduction of signals from the cortical neurons to the scalp where they are measured, where each electrode captures electrical activity from neurons located near the other adjacent electrode.

The obscuring of measurement results due to volume conduction or cross-talk is known as volume conduction artifact. By using an infant subject, volume conduction artifact is reduced relative to an adult subject, due to the relative thinness of the infant's skull. In some embodiments, of the invention, volume conduction artifact is further reduced by using an artifact reduction algorithm or mathematical technique, as referenced in FIG. 1 and explained further below. By sufficiently reducing volume conduction artifact and using many closely spaced (3 centimeters apart or less) electrodes, local synchrony information can be obtained from EEG information.

Figure 3:
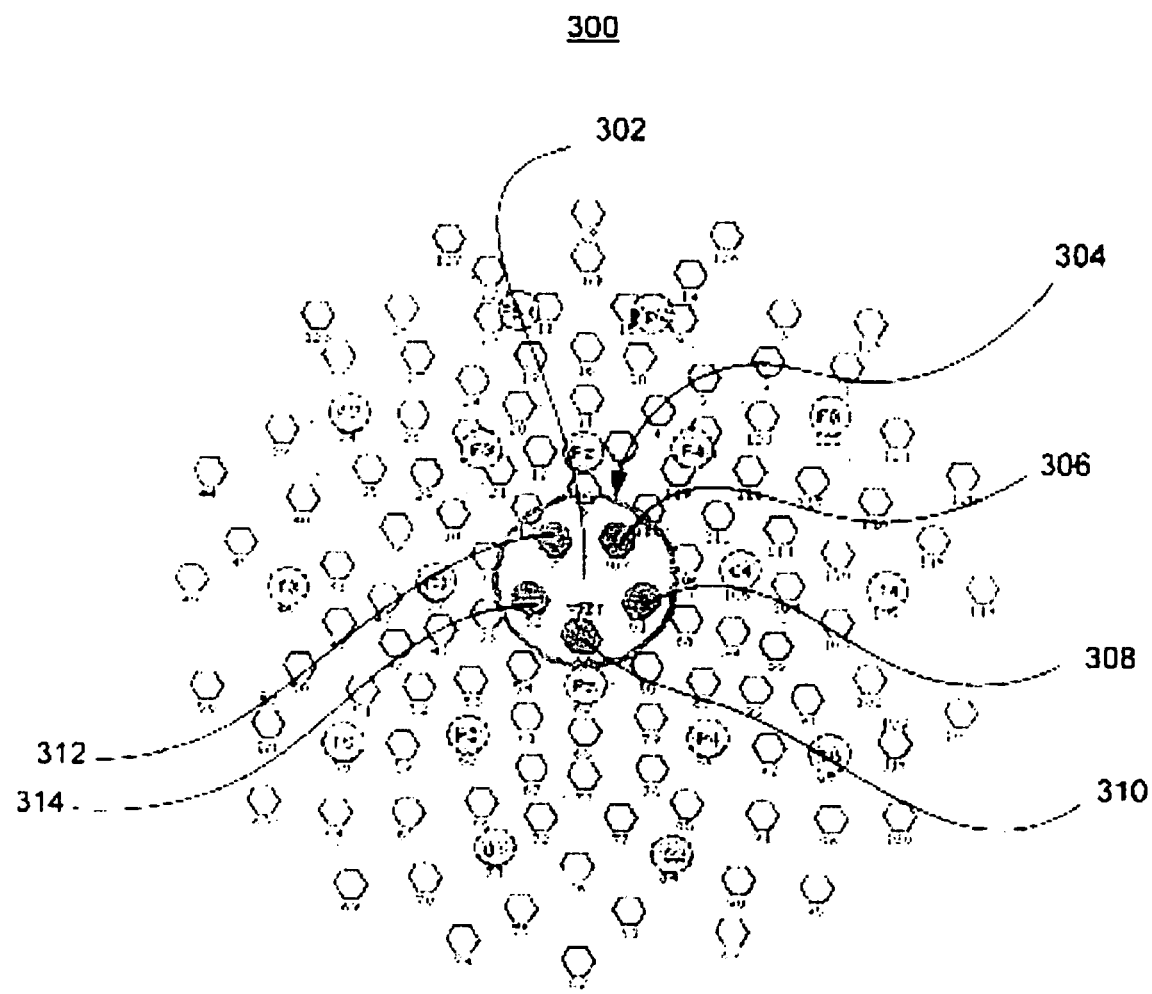
FIG. 3 is a block diagram depicting a technique for collecting EEG information used to obtain local synchrony information, and local synchrony, according to one embodiment of the invention.

FIG. 3 is a block diagram depicting a technique for collecting EEG information used to obtain local synchrony information, and local synchrony, according to one embodiment of the invention. Specifically, FIG. 3 shows how an 128 channel electrode array collects data suitable for the collection of EEG data suitable for measurement of local synchrony. In FIG. 1, local coherence at electrode 304 is computed as the average of the coherence values for the electrode 304 with its surrounding electrodes 306, 308, 310, 312, 314. This process is done for every electrode in the array to produce a spatial map of local coherence values at every electrode position. The spatial area including the electrodes 304, 306, 308, 310, 312, 314 is indicated as area 302.

Figure 4A:
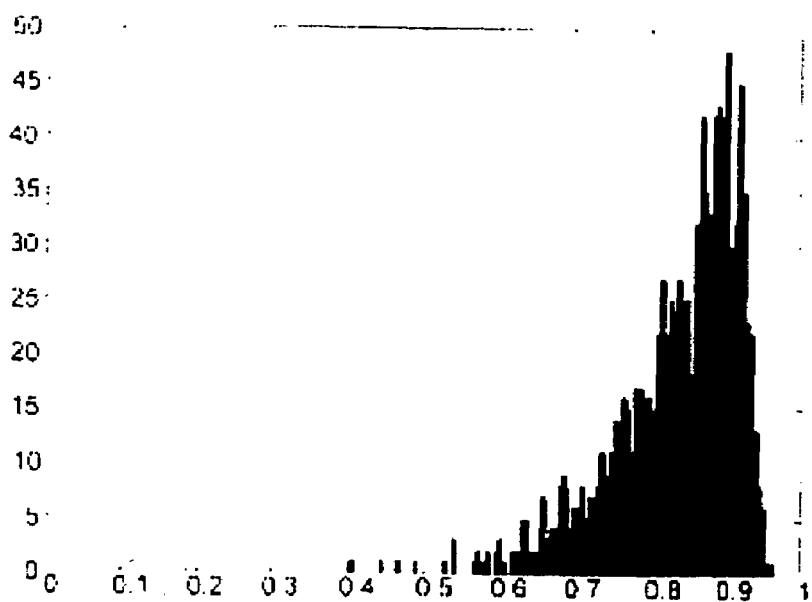
FIG. 4A depicts a histogram of local coherence values for 15 newborn infants.
Figure 4B:
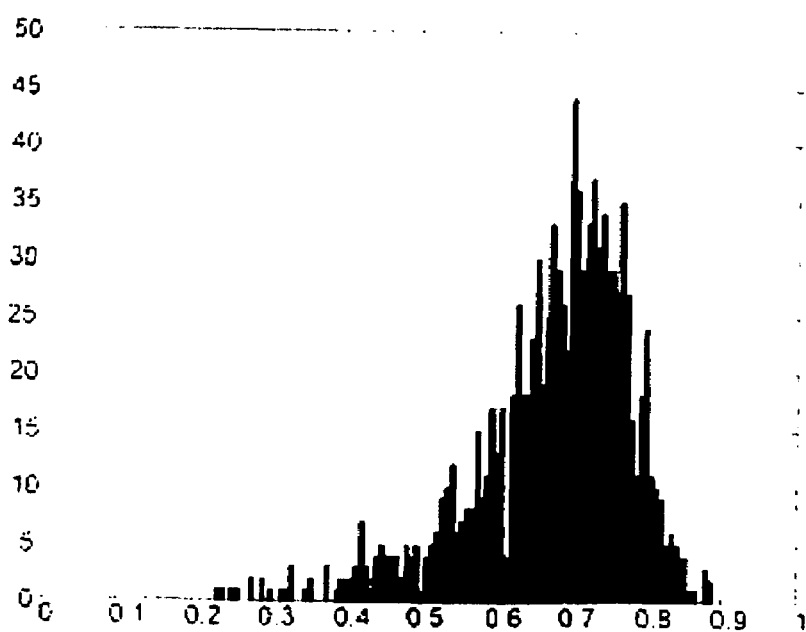
FIG. 4B depicts a histogram of local coherence values for 15 newborn infants after reducing residual volume conduction effects.

FIG. 4A depicts a histogram of local coherence values for 15 newborn infants. The presence of volume conduction is manifested by the skew of the values towards the highest coherence values and the lack of low coherence values. FIG. 4B depicts the data after processing with the method described above to remove or reduce residual volume conduction effects. The data is seen shifted to lower coherence values and includes smaller values of the coherence than in FIG. 4A. The data depicted in FIG. 4B is more accurate than that depicted in FIG. 4A. The inaccurate shifting to the right in FIG. 4A results from volume conduction artifact which skews the data depicted in FIG. 4A.

Figure 5:
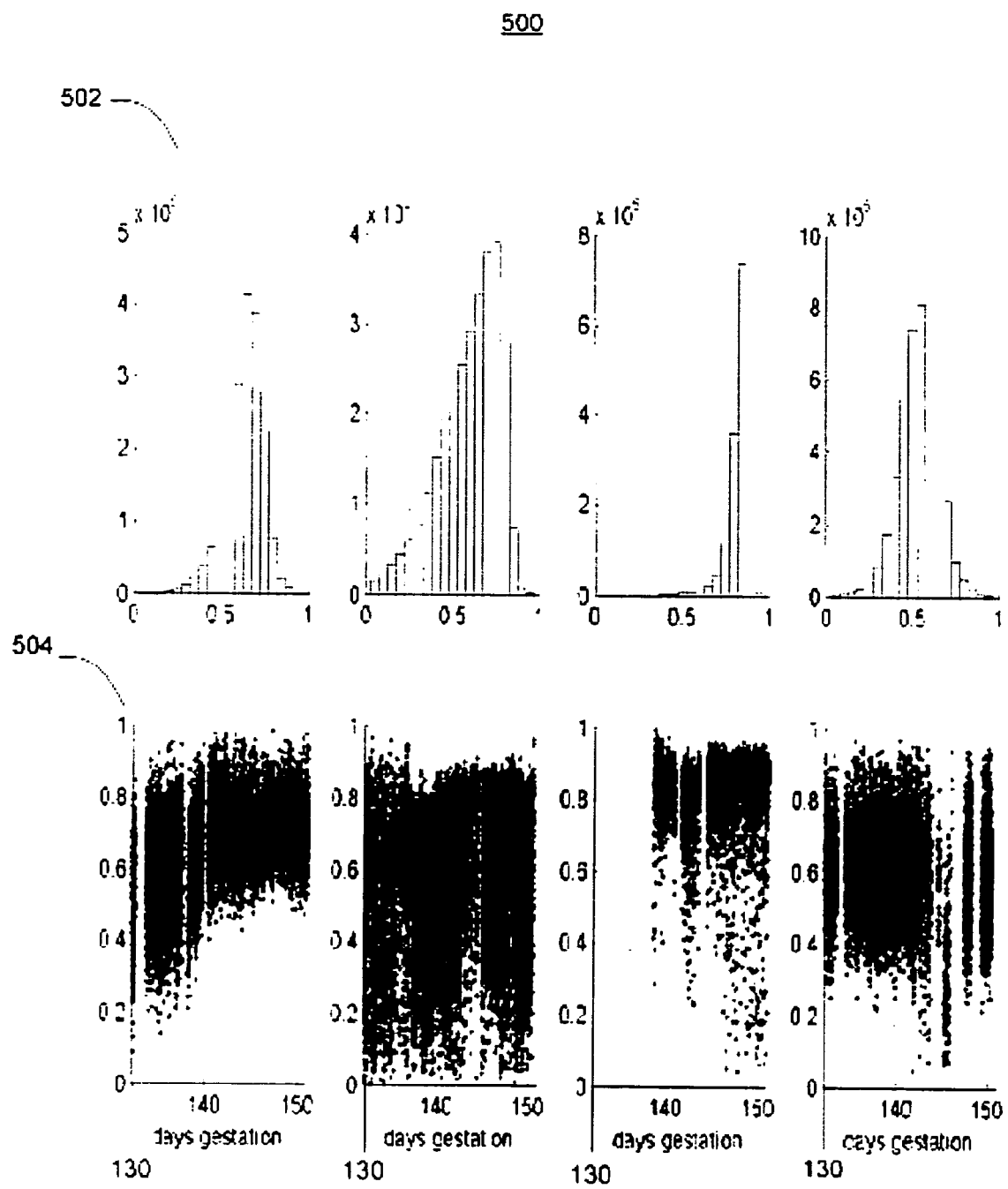
FIG. 5 depicts histograms of local coherence and corresponding graphical data, obtained using a method according to some embodiments of the invention.

FIG. 5 depicts histograms of local coherence and corresponding graphical data, obtained according to some embodiments of the invention. Upper row 502 is a collection of histograms of local coherence obtained from electrodes placed on the dura but below the skull of 4 fetal baboons, and lower row 504 depicts associated data points. This data was collected over a period of approximately 130-150 days of gestation and is also shown as a scatter plot (local coherence vs. gestational age) in the bottom row of the figure. These local coherence values have little or no volume conduction error because of the electrode placement below the skull. Note the similarity of these histograms to that of FIG. 4B. This shows that the volume conduction removal algorithm has produced local coherence values similar to that obtained with EEG electrodes place on or near the brain's surface.

Figure 6:
FIG. 6 is a graphical representation of the results of the measurement of changes in regional local coherence, according to one embodiment of the invention.
Figure 6:
Figure 6:
Figure 6:
Figure 6:
Figure 6:
Figure 6:
Figure 6:
Figure 6:
Figure 6:
Figure 6:

FIG. 6 is a graphical representation of the results of the measurement of changes in regional local coherence in 15 newborn infants as a result of a head-up body tilt, as determined using local synchronization information obtained using a method according to one embodiment of the invention. The dark areas indicate regions of the brain determined to have a higher local coherence as compared to pre-tilt values in the same region. Specifically, The dark regions are clusters of electrodes for which the percent change due to tilt in local coherence was significant at the $p<0.02$ level (two sided t-test).

Column 602 is a graphical representation showing the regions of activation when no correction for volume conduction in local coherence was made. Column 604 shows the regions of activation when volume conduction error was corrected for in the computation of local coherence, using a method according to one embodiment of the invention. In each panel, a frontal and a posterior region were found. The regions are very similar in location and size.

Figure 7:
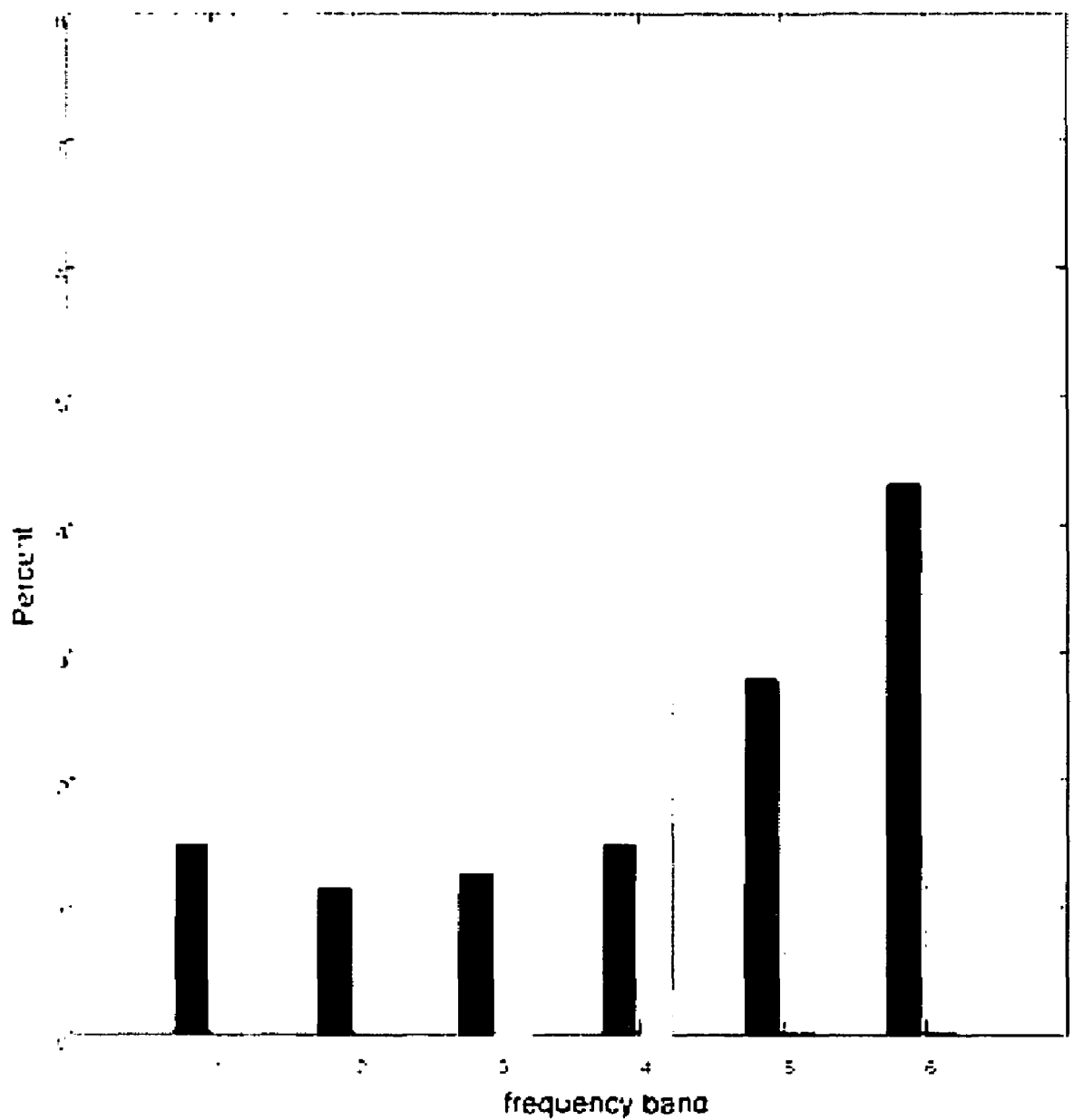
FIG. 7 is a bar graph showing the average change score for frontal brain region local coherence, computed with and without the correction for volume conduction in the calculation of local coherence, according to one embodiment of the invention.
Figure 8:
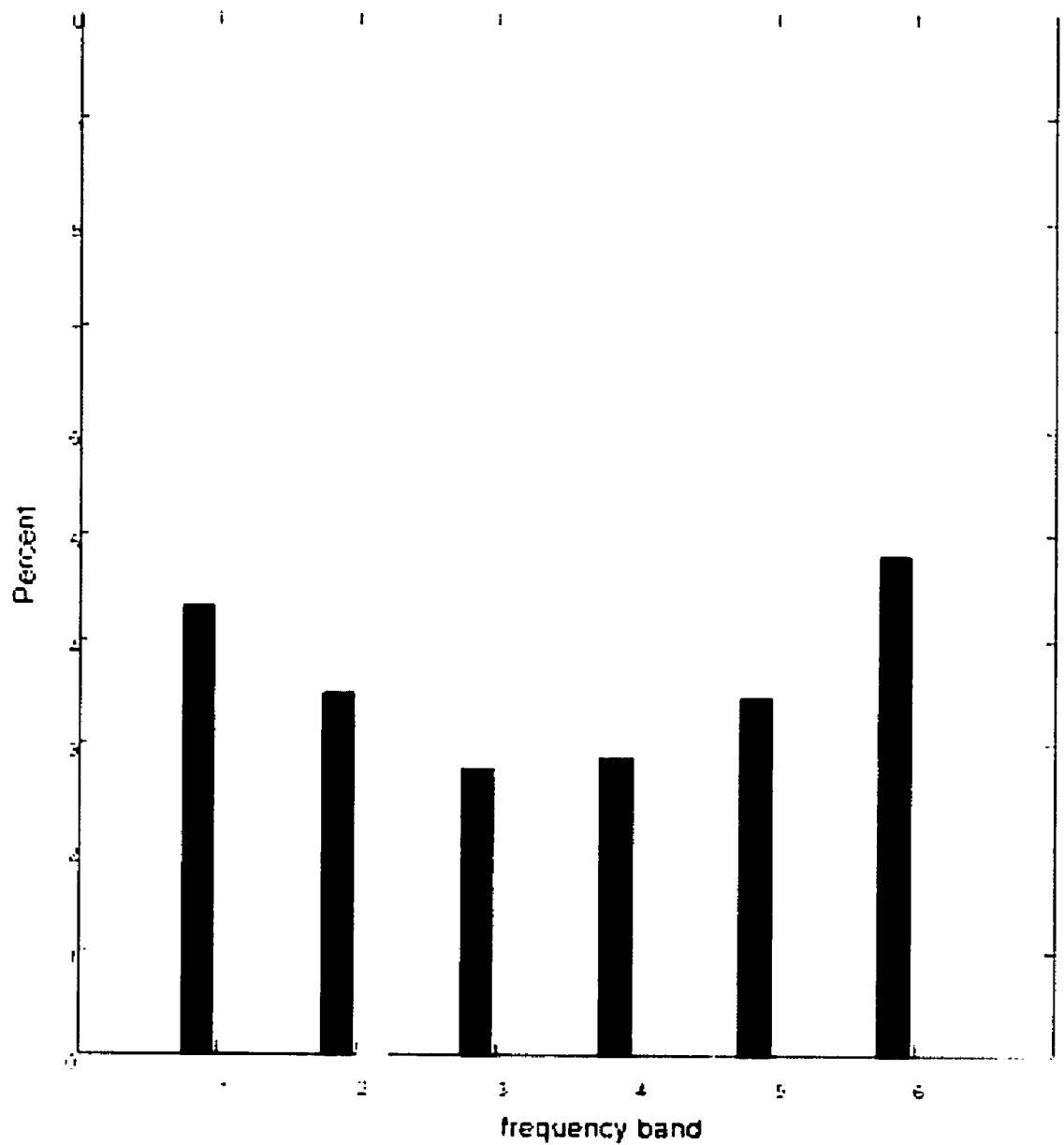
FIG. 8 is a bar graph showing the average change score for posterior brain region local coherence, computed with and without the correction for volume conduction in the calculation of local coherence, according to one embodiment of the invention.

FIGS. 7 and 8 are bar graphs showing the average change score for each region (frontal and posterior, respectively) computed with and without the correction for volume conduction in the calculation of local coherence. The darker bars are the percent changes of local coherence in 6 frequency bands in the two spatial regions that were significant without correction for volume conduction. The lighter bars are the same raw data but processed with an algorithm to remove volume conduction according to one embodiment of the invention, and averaged over the significant regions obtained when volume conduction was corrected for. As depicted, the lighter bars are larger than the darker bars, indicating that removal of volume conduction makes the local coherence measurement more sensitive to the change in neural activation.

FIGS. 9-12 are flow charts depicting some embodiments of the invention.

With reference to the flow diagram 900 of FIG. 9, at step 902, EEG information is obtained. At step 904, the EEG information is processed to obtain local synchrony.

With reference to the flow diagram 1000 of FIG. 10, at step 1002, EEG information is obtained from an infant subject. At step 1004, the EEG information is processed to obtain local synchrony information.

With reference to the flow diagram 1100 of FIG. 11, at step 1102, EEG information is obtained. At step 1104, the EEG information is processed to obtain local synchrony information using a volume conduction artifact reduction algorithm.

With reference to the flow diagram 1200 of FIG. 12, at step 1202, EEG information is obtained from an infant subject. At step 1204, the EEG information is processed to obtain local synchrony information using a volume conduction artifact reduction algorithm.

In some embodiments of the invention, a mathematical technique, mathematical algorithm, or computer algorithm is used to reduce volume conduction artifact in EEG information from infant subjects, allowing determination of a measure of average local synchrony and local coherence. It is to be understood, however, that in some embodiments, the mathematical technique or algorithm is applied to reduce volume conduction artifact in adult EEG information. The relatively small amount of volume conduction present in the infant EEG as compared with adult EEG, however, makes possible the development of an uncomplicated data processing algorithm that can reduce the contamination of the coherence measurement by volume conduction.

In the electrode geometry shown in FIG. 1, each electrode is surrounded by nearest neighbors. Consider now the computation of EEG synchrony between the central electrode and a neighboring electrode. Each electrode measures a voltage component from cortical neurons in its immediate vicinity and also from the volume conduction of neural activity in the vicinity of the other electrode. The volume conducted voltages are reduced in amplitude because of the spread of current in the head. Thus one can model the time varying voltages at two electrodes as:

$$V_t = x_t + \alpha y_t + n_{xt}$$

$$U_t = y_t + \alpha x_t + n_{yt} \tag{1}$$

where $x_t$ and $y_t$ are the voltages from local neural activity at each of the two electrodes, $\alpha$ is the small fraction of voltage volume conducted from the local region to the region of the remote electrode, and $n_{xt}$ and $n_{yt}$ are noise random processes that uncorrelated with the neural activity. The noise random processes represent electrical activity of scalp muscle and amplifier noise. The coherence function for the electrode voltages is defined as:

$$\gamma_{vu} = \frac{S_{vu}}{\sqrt{S_{vv} S_{uu}}} \tag{2}$$

where the "S" denotes the self spectral and cross spectral density functions for the electrode voltages. Inserting (1) into (2) yields:

$$\gamma_{vu} = \frac{\left(\gamma_{xy} + \alpha^2 \gamma_{yx} + \alpha\left(\sqrt{\frac{S_{yy}}{S_{xx}}} + \sqrt{\frac{S_{yy}}{S_{xx}}}\right)\right)}{\sqrt{\left(1 + 2\alpha \Re e(\gamma_{xy})\sqrt{\frac{S_{xx}}{S_{yy}}} + \alpha^2 \frac{S_{xx}}{S_{yy}} + \frac{S_{ny}}{S_{yy}}\right)\left(1 + 2\alpha \Re e(\gamma_{xy})\sqrt{\frac{S_{yy}}{S_{xx}}} + \alpha^2 \frac{S_{yy}}{S_{xx}} + \frac{S_{nx}}{S_{xx}}\right)}} \tag{3}$$

Note that contributions from neural activity at regions other than those in the vicinity of the two electrodes being considered will also produce contributions to the electrode voltages of (1). However as these voltage components are the result of volume conduction their contributions will be multiplied by a small parameter similar in magnitude to $\alpha$, their contribution to the coherence of (2) will be of second order in this parameter and thus their contribution can be neglected in (3). Thus, to a first order, it is possible to deal with interactions between each pair of electrodes separately. This assumption greatly simplifies the method.

Equation (3) relates the measured coherence, $\gamma_{vu}$, that contains errors from volume conduction and additive noise, to the error-free coherence $\gamma_{xy}$. Dropping terms of second order in $\alpha$ and equating real and imaginary components yields:

$$\Re e(\gamma_{vu}) = \frac{\Re e(\gamma_{xy}) + \alpha\left(\sqrt{\frac{S_{yy}}{S_{xx}}} + \sqrt{\frac{S_{yy}}{S_{xx}}}\right)}{\sqrt{\left(1 + 2\alpha \Re e(\gamma_{xy})\sqrt{\frac{S_{xx}}{S_{yy}}} + \frac{S_{ny}}{S_{yy}}\right)\left(1 + 2\alpha \Re e(\gamma_{xy})\sqrt{\frac{S_{yy}}{S_{xx}}} + \frac{S_{nx}}{S_{xx}}\right)}} \tag{4}$$

$$\Im m(\gamma_{vu}) = \frac{\Im m(\gamma_{xy})}{\sqrt{\left(1 + 2\alpha \Re e(\gamma_{xy})\sqrt{\frac{S_{xx}}{S_{yy}}} + \frac{S_{ny}}{S_{yy}}\right)\left(1 + 2\alpha \Re e(\gamma_{xy})\sqrt{\frac{S_{yy}}{S_{xx}}} + \frac{S_{nx}}{S_{xx}}\right)}} \tag{5}$$

These equations can be solved for $\gamma_{xy}$ (for each frequency value) by solving for $\Re e(\gamma_{xy})$ in the quadratic equation (4) and then substituting that result into (5) to solve for $\Im m(\gamma_{xy})$. The signal and noise spectral density functions are measured as follows. The measured average EEG spectral density in a high frequency band (e.g. 350-400 Hz) in each channel is assumed to be equal to the noise spectral density level as the power spectrum of the cerebral component of the EEG is known to decrease rapidly with increasing frequency. The spectral densities $S_{xx}$ and $S_{yy}$ are then found for use in the equation, to a first order in $\alpha$, by subtracting the noise spectral densities from the measured spectral densities $S_{uu}$ and $S_{vv}$. The value of $\alpha$, the volume conduction parameter, is found as follows. When $\gamma_{xy}=0$, and ignoring second order terms in $\alpha$, (3) yields.

$$\gamma_{vu} = \frac{\alpha\left(\sqrt{\frac{S_{yy}}{S_{xx}}} + \sqrt{\frac{S_{yy}}{S_{xx}}}\right)}{\sqrt{\left(1 + \frac{S_{ny}}{S_{yy}}\right)\left(1 + \frac{S_{nx}}{S_{xx}}\right)}} \tag{6}$$

This result shows that volume conduction places a lower bound on the measured coherence value. In Grieve, et al. (2003), previously incorporated by reference, this lower bound is calculated with electromagnetic theory using reasonable assumptions for the head's anatomy and passive electrical properties. The value is independent of frequency. The key parameter of this analysis is the thickness of the skull. Thus in (6) we replace $\gamma_{vu}$ by the lower bound calculated in Grieve, et al. (2003) for a skull thickness equal to that appropriate for the subject. Then the value of $\alpha$ is solved for from (6). This technique for correction of the errors in the measured coherence is carried out for every measurement frequency. Thus the value for $\alpha$, which should theoretically be independent of frequency, is calculated for each frequency, for use in the correction of measured coherence. It has been found that the values calculated for α over frequency are nearly identical. This consistency forms a basis of validation for the above-described techniques.

Figure 13:
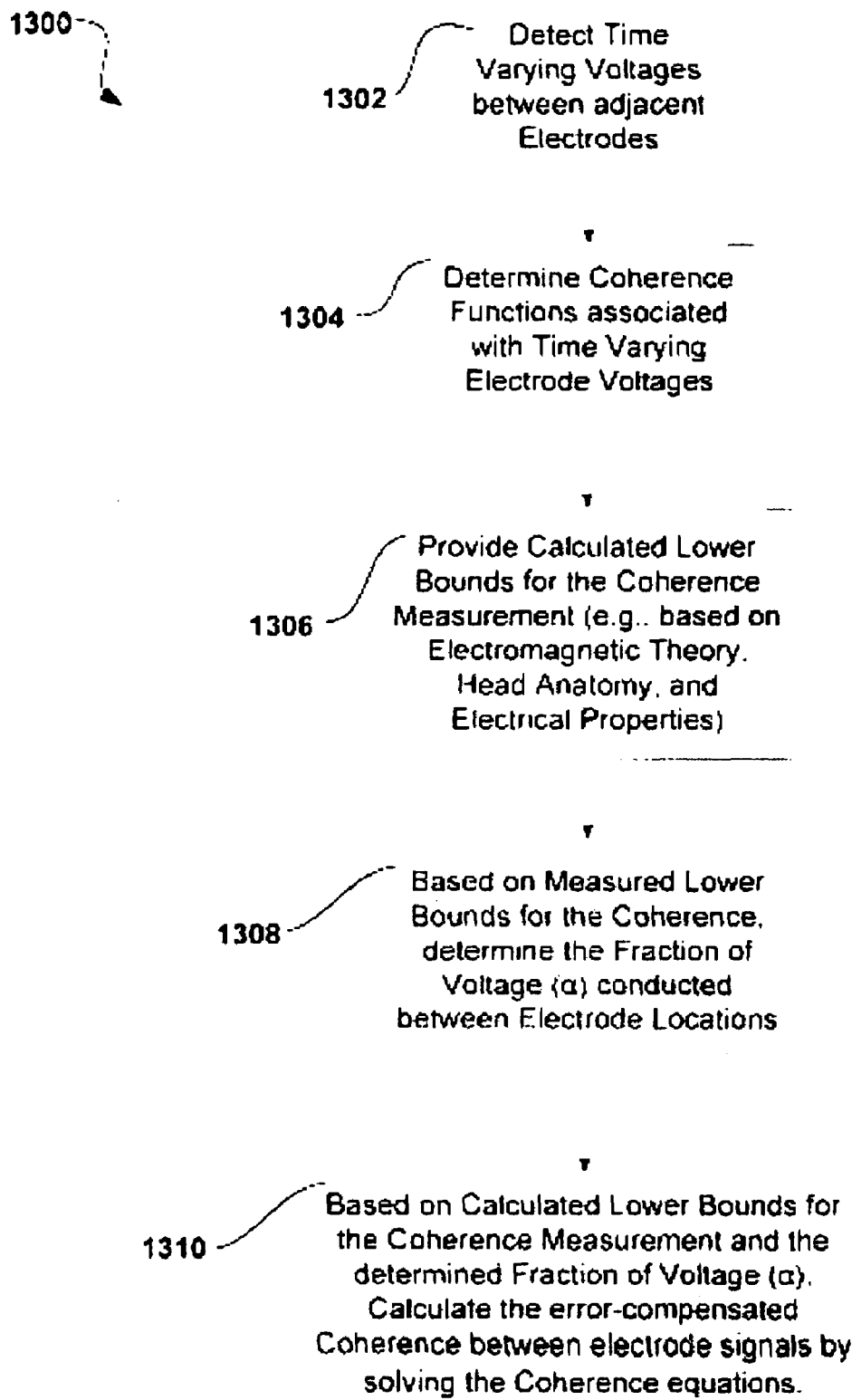
FIG. 13 is a flow diagram depicts a method for calculating error-compensated coherence, according to one embodiment of the invention.

FIG. 13 depicts a method 1300 for calculating error compensated coherence, according to one embodiment of the invention. In some embodiments, the method 1300 is performed using a mathematical technique or algorithm in accordance with some embodiments of the invention (as depicted with reference to FIG. 1).

At step 1302, varying voltages are detected between adjacent electrodes.

At step 1304, the algorithm is used in determining coherence functions based on time varying electrode voltages.

At step 1306, the algorithm is used in calculating lower bounds for coherence measurements (e.g., based on electromagnetic theory, head anatomy and/or electrical properties).

At step 1308, the algorithm is used in, based on measured lower bounds for the coherence, determining the fraction of voltage (α). At step 1310, the algorithm is used in, based on calculated lower bounds for the coherence measurement and the determined fraction of voltage (α), calculating the error-compensated coherence between electrode signals by solving the coherence equations.

What is claimed is:

1. A system for obtaining local synchrony information, the system comprising:
   an EEG device for obtaining EEG information, the device comprising a plurality of electrodes placed to measure a subject's brain electrical activity; and
   a processing device for processing the EEG information to obtain information including local synchrony information, wherein the processing device is configured to execute a computer algorithm to reduce residual volume conduction artifact in the obtained local synchrony information.

2. The system of claim 1, wherein the local synchrony information includes local coherence information.

3. The system of claim 1, comprising a plurality of electrodes for scalp placement.

4. The system of claim 1, comprising a plurality of electrodes for scalp placement on an infant subject.

5. The system of claim 4, wherein adjacent electrodes of the plurality of electrodes are spaced no more than 1 centimeter apart.

6. The system of claim 4, wherein adjacent electrodes of the plurality of electrodes are spaced no more than 3 millimeters apart.

7. The system of claim 4, wherein the plurality of electrodes includes at least 100 electrodes.

8. The system of claim 4, wherein the obtained local synchrony information is used in spatial mapping of local regional brain activity.

9. The system of claim 4, wherein the obtained local synchrony information is used in at least one of researching brain function, evaluating brain function, and diagnosing a medical condition.

10. The system of claim 4, comprising:
   a plurality of transducer devices for receiving neuron electrical activity, wherein the plurality of transducer devices are distributed over the scalp surface for generating electrical signals based on the received neuron electrical activity wherein the processing devicer is configured to calculate a coherence function between the generated electrical signal associated with at least two of the plurality of transducer devices that are adjacently located, wherein the coherence function at least partially compensates for residual volume conduction relating to corresponding adjacent electrical signals associated with the at least two of the plurality of transducer devices.

11. The system of claim 10, wherein the computer algorithm utilizes an error-free coherence function.

12. The system of claim 10, wherein the computer algorithm that solves for the true coherence function with reduced volume conductions artifact, $\gamma_{xy}$, using the equations:

$$\Re e(\gamma_{vu}) = \frac{\Re e(\gamma_{xy}) + \alpha\left(\sqrt{\frac{S_{yy}}{S_{xx}}} + \sqrt{\frac{S_{yy}}{S_{xx}}}\right)}{\sqrt{\left(1 + 2\alpha \Re e(\gamma_{xy})\sqrt{\frac{S_{xx}}{S_{yy}}} + \frac{S_{ny}}{S_{yy}}\right)\left(1 + 2\alpha \Re e(\gamma_{xy})\sqrt{\frac{S_{yy}}{S_{xx}}} + \frac{S_{nx}}{S_{xx}}\right)}}$$

$$\Im m(\gamma_{vu}) = \frac{\Im m(\gamma_{xy})}{\sqrt{\left(1 + 2\alpha \Re e(\gamma_{xy})\sqrt{\frac{S_{xx}}{S_{yy}}} + \frac{S_{ny}}{S_{yy}}\right)\left(1 + 2\alpha \Re e(\gamma_{xy})\sqrt{\frac{S_{yy}}{S_{xx}}} + \frac{S_{nx}}{S_{xx}}\right)}}$$

Wherein S represents spectral density functions for and between adjacent electrode signals and α is a volume conduction parameter obtained from $$\gamma_{vu} = \frac{\alpha\left(\sqrt{\frac{S_{yy}}{S_{xx}}} + \sqrt{\frac{S_{yy}}{S_{xx}}}\right)}{\sqrt{\left(1 + \frac{S_{ny}}{S_{yy}}\right)\left(1 + \frac{S_{nx}}{S_{xx}}\right)}}.$$

13. A method for obtaining local synchrony information, the method comprising: obtaining EEG information; and using the obtained EEG information, obtaining local synchrony information; wherein obtaining EEG information comprises using a mathematical technique to reduce residual volume conduction artifact in the obtained local synchrony information.

14. The method of claim 13, wherein obtaining local synchrony information further comprises obtaining local coherence information.

15. The method of claim 13, comprising obtaining the EEG information using electrodes placed on a subject's scalp.

16. The method of claim 13, comprising obtaining the EEG information using electrodes placed on an infant subject's scalp.

17. The method of claim 13, comprising obtaining the EEG information comprises using electrodes spaced no more than 1 centimeter apart.

18. The method of claim 13, comprising obtaining the EEG information comprises using electrodes spaced no more than 3 millimeters apart.

19. The method of claim 13, comprising obtaining the EEG information using at least 100 electrodes.

20. A method for obtaining local synchrony information, the method comprising: obtaining EEG information from an infant subject; and using the obtained EEG information, obtaining local synchrony information; wherein obtaining EEG information comprises using a mathematical technique to reduce residual volume conduction artifact in the obtained local synchrony information.

21. The method of claim 20, wherein obtaining the local synchrony information further comprises obtaining local coherence information.

22. The method of claim 20, comprising using a computer algorithm to employ the mathematical technique.

23. The method of claim 20, comprising obtaining local synchrony information relating to adjacent brain regions.

24. The method of claim 20, comprising using the local synchrony in evaluating brain function.

25. The method of claim 20, comprising using the local synchrony information in spatial mapping of local regional brain activity.

26. The method of claim 20, comprising using the local synchrony information in at least one of researching brain function, evaluating brain function, and diagnosing a medical condition.

27. The method of claim 20, comprising: measuring a first EEG signal from a first region on a scalp; measuring a second EEG signal from a second region on the scalp, wherein the first and the second region are substantially adjacent one another; and using the mathematical technique, determining a coherence function between the first electroencephalogram signal and the second electroencephalogram signal such that the coherence function can be used in at least partially compensating for a first fractional signal conducted from the first region of the scalp to the second region of the scalp and a second fractional signal conducted from the second region of the scalp to the first region of the scalp.

28. The method of claim 20, wherein the mathematical technique obtains an error-free coherence function, $\gamma_{xy}$, from the equations:

$$\Re e(\gamma_{vu}) = \frac{\Re e(\gamma_{xy}) + \alpha\left(\sqrt{\frac{S_{yy}}{S_{xx}}} + \sqrt{\frac{S_{yy}}{S_{xx}}}\right)}{\sqrt{\left(1 + 2\alpha\Re e(\gamma_{xy})\sqrt{\frac{S_{xx}}{S_{yy}}} + \frac{S_{ny}}{S_{yy}}\right)\left(1 + 2\alpha\Re e(\gamma_{xy})\sqrt{\frac{S_{yy}}{S_{xx}}} + \frac{S_{nx}}{S_{xx}}\right)}}$$

$$\Im m(\gamma_{vu}) = \frac{\Im m(\gamma_{xy})}{\sqrt{\left(1 + 2\alpha\Re e(\gamma_{xy})\sqrt{\frac{S_{xx}}{S_{yy}}} + \frac{S_{ny}}{S_{yy}}\right)\left(1 + 2\alpha\Re e(\gamma_{xy})\sqrt{\frac{S_{yy}}{S_{xx}}} + \frac{S_{nx}}{S_{xx}}\right)}}$$

Wherein S represents spectral density functions for and between adjacent electrode signals and $\alpha$ is a volume conduction parameter obtained from $$\gamma_{vu} = \frac{\alpha\left(\sqrt{\frac{S_{yy}}{S_{xx}}} + \sqrt{\frac{S_{yy}}{S_{xx}}}\right)}{\sqrt{\left(1 + \frac{S_{ny}}{S_{yy}}\right)\left(1 + \frac{S_{nx}}{S_{xx}}\right)}}.$$

29. The method of claim 20, wherein the computer algorithm utilizes a coherence function obtained from the equations:

$$\Re e(\gamma_{vu}) = \frac{\Re e(\gamma_{xy}) + \alpha\left(\sqrt{\frac{S_{yy}}{S_{xx}}} + \sqrt{\frac{S_{yy}}{S_{xx}}}\right)}{\sqrt{\left(1 + 2\alpha\Re e(\gamma_{xy})\sqrt{\frac{S_{xx}}{S_{yy}}} + \frac{S_{ny}}{S_{yy}}\right)\left(1 + 2\alpha\Re e(\gamma_{xy})\sqrt{\frac{S_{yy}}{S_{xx}}} + \frac{S_{nx}}{S_{xx}}\right)}}$$

$$\Im m(\gamma_{vu}) = \frac{\Im m(\gamma_{xy})}{\sqrt{\left(1 + 2\alpha\Re e(\gamma_{xy})\sqrt{\frac{S_{xx}}{S_{yy}}} + \frac{S_{ny}}{S_{yy}}\right)\left(1 + 2\alpha\Re e(\gamma_{xy})\sqrt{\frac{S_{yy}}{S_{xx}}} + \frac{S_{nx}}{S_{xx}}\right)}}$$

Wherein S represents spectral density functions for and between adjacent electrode signals and $\alpha$ is a volume conduction parameter obtained from $$\gamma_{vu} = \frac{\alpha\left(\sqrt{\frac{S_{yy}}{S_{xx}}} + \sqrt{\frac{S_{yy}}{S_{xx}}}\right)}{\sqrt{\left(1 + \frac{S_{ny}}{S_{yy}}\right)\left(1 + \frac{S_{nx}}{S_{xx}}\right)}}.$$

30. The method of claim 20, wherein the subject is a person.

31. The method of claim 20, wherein the subject is an animal.

* * * * *